(12) United States Patent
Laugharn, Jr. et al.

(10) Patent No.: US 7,757,561 B2
(45) Date of Patent: Jul. 20, 2010

(54) METHODS AND SYSTEMS FOR PROCESSING SAMPLES USING ACOUSTIC ENERGY

(75) Inventors: James A. Laugharn, Jr., Winchester, MA (US); Brevard S. Garrison, Reading, MA (US); Douglas A. Yates, North Andover, MA (US)

(73) Assignee: Covaris, Inc., Woburn, MA (US)

( * ) Notice: Subject to any disclaimer, the term of this patent is extended or adjusted under 35 U.S.C. 154(b) by 720 days.

(21) Appl. No.: 11/497,865

(22) Filed: Aug. 1, 2006

(65) Prior Publication Data
US 2007/0053795 A1   Mar. 8, 2007

Related U.S. Application Data

(60) Provisional application No. 60/704,794, filed on Aug. 1, 2005, provisional application No. 60/715,660, filed on Sep. 9, 2005.

(51) Int. Cl.
*B01F 11/02* (2006.01)
*B06B 1/00* (2006.01)

(52) U.S. Cl. .................. 73/644; 366/127; 366/145; 422/128

(58) Field of Classification Search ............ 73/644, 73/602; 422/128; 366/127, 145
See application file for complete search history.

(56) References Cited

U.S. PATENT DOCUMENTS 1,734,975 A   11/1929 Loomis et al.
2,447,061 A   8/1948 Franklin
2,565,159 A   8/1951 Williams
2,578,505 A   12/1951 Carlin
2,585,103 A   2/1952 Fitzgerald
2,632,634 A   3/1953 Williams
2,738,172 A   3/1956 Spiess, Jr. et al.
2,855,526 A   10/1958 Jones
2,864,592 A   12/1958 Camp
2,916,265 A   12/1959 Towne
2,950,725 A   8/1960 Jacke et al.
3,066,686 A   12/1962 O'Neill
3,194,640 A   7/1965 Nesh
3,292,910 A   12/1966 Martner (Continued)

FOREIGN PATENT DOCUMENTS

DE   2557668 A1   6/1977

(Continued)

OTHER PUBLICATIONS

Notice of Allowance from related U.S. Appl. No. 11/006,002.

(Continued)

*Primary Examiner*—Hezron Williams
*Assistant Examiner*—Rose M Miller
(74) *Attorney, Agent, or Firm*—Wolf, Greenfield & Sacks, P.C.

(57) ABSTRACT

Methods and systems for automated compound management and sample preparation using acoustic energy. In some embodiments, acoustic energy may be transmitted through a medium and a solid or semi-solid layer that is disposed adjacent to the vessel. Both the medium and the solid or semi-solid layer may couple acoustic energy from an acoustic energy source to a focal zone in close proximity to the sample in the vessel.

39 Claims, 9 Drawing Sheets

U.S. PATENT DOCUMENTS

| | | |
|---|---|---|
| 3,396,286 A | 8/1968 | Anderson et al. |
| 3,481,186 A | 12/1969 | Plofsky et al. |
| 3,604,270 A | 9/1971 | Falk |
| 3,614,069 A | 10/1971 | Murry |
| 3,743,523 A | 7/1973 | Bodine |
| 3,807,704 A | 4/1974 | Janzen et al. |
| 3,837,805 A | 9/1974 | Boucher |
| 3,876,890 A | 4/1975 | Brown et al. |
| 3,919,558 A | 11/1975 | Brouillette et al. |
| 4,028,933 A | 6/1977 | Lemons et al. |
| 4,059,098 A * | 11/1977 | Murdock ............ 600/437 |
| 4,307,964 A | 12/1981 | Dudgeon et al. |
| RE31,779 E | 12/1984 | Alliger |
| 4,488,816 A | 12/1984 | Vota et al. |
| 4,541,281 A | 9/1985 | Chubachi et al. |
| 4,571,087 A | 2/1986 | Ranney |
| 4,644,808 A | 2/1987 | Lecoffre |
| 4,764,905 A | 8/1988 | Granz et al. |
| 4,834,124 A | 5/1989 | Honda et al. |
| 4,862,060 A | 8/1989 | Scott et al. |
| 4,879,011 A | 11/1989 | Schram |
| 4,889,122 A | 12/1989 | Watmough et al. |
| 4,926,871 A | 5/1990 | Ganguly et al. |
| 4,983,189 A | 1/1991 | Peterson et al. |
| 5,026,167 A | 6/1991 | Berliner, III |
| 5,037,481 A | 8/1991 | Bran |
| 5,368,054 A | 11/1994 | Koretsky et al. |
| 5,395,592 A | 3/1995 | Bolleman et al. |
| 5,409,594 A | 4/1995 | Al-Jiboory et al. |
| 5,484,573 A | 1/1996 | Berger et al. |
| 5,509,420 A * | 4/1996 | Ohtomo et al. ............ 600/445 |
| 5,523,058 A | 6/1996 | Umemura et al. |
| 5,585,565 A * | 12/1996 | Glascock et al. ............ 73/644 |
| 5,601,526 A | 2/1997 | Chapelon et al. |
| 5,623,095 A | 4/1997 | Beller |
| 5,631,425 A | 5/1997 | Wang et al. |
| 5,639,423 A | 6/1997 | Northrup et al. |
| 5,681,396 A | 10/1997 | Madanshetty |
| 5,688,406 A | 11/1997 | Dickinson et al. |
| 5,736,100 A | 4/1998 | Miyake et al. |
| 5,759,162 A | 6/1998 | Oppelt et al. |
| 5,779,985 A | 7/1998 | Sucholeiki |
| 5,803,099 A | 9/1998 | Sakuta et al. |
| 5,831,166 A | 11/1998 | Kozuka et al. |
| 5,834,648 A | 11/1998 | Wang et al. |
| 5,890,802 A | 4/1999 | Evensen et al. |
| 5,962,338 A | 10/1999 | Sucholeiki |
| 5,993,671 A | 11/1999 | Peltzer |
| 6,003,388 A | 12/1999 | Oeftering |
| 6,010,316 A | 1/2000 | Haller et al. |
| 6,039,309 A | 3/2000 | Kuklinski |
| 6,039,694 A * | 3/2000 | Larson et al. ............ 600/459 |
| 6,042,556 A | 3/2000 | Beach et al. |
| 6,086,821 A | 7/2000 | Lee |
| 6,100,084 A | 8/2000 | Miles et al. |
| 6,210,128 B1 | 4/2001 | Rife et al. |
| 6,224,778 B1 | 5/2001 | Peltzer |
| 6,244,738 B1 | 6/2001 | Yasuda et al. |
| 6,277,332 B1 | 8/2001 | Sucholeiki |
| 6,284,113 B1 | 9/2001 | Bjornson et al. |
| 6,291,180 B1 | 9/2001 | Chu |
| 6,361,747 B1 | 3/2002 | Dion et al. |
| 6,413,783 B1 | 7/2002 | Wohlstadter et al. |
| 6,440,725 B1 | 8/2002 | Pourahmadi et al. |
| 6,515,030 B1 | 2/2003 | Bechtel et al. |
| 6,591,680 B2 * | 7/2003 | Batzinger et al. ............ 73/598 |
| 6,627,421 B1 * | 9/2003 | Unger et al. ............ 435/173.5 |
| 6,699,711 B1 * | 3/2004 | Hahn et al. ............ 435/283.1 |
| 6,719,449 B1 | 4/2004 | Laugharn, Jr. et al. |
| 6,737,021 B2 | 5/2004 | Watari et al. |
| 6,948,843 B2 | 9/2005 | Laugharn, Jr. et al. |
| 7,211,927 B2 | 5/2007 | Puskas |
| 7,297,311 B2 * | 11/2007 | Tamura et al. ............ 422/63 |
| 7,329,039 B2 | 2/2008 | Laugharn, Jr. et al. |
| 7,521,023 B2 | 4/2009 | Laugharn et al. |
| 2002/0082527 A1 * | 6/2002 | Liu et al. ............ 601/2 |
| 2003/0005771 A1 * | 1/2003 | Percin et al. ............ 73/627 |
| 2003/0165482 A1 | 9/2003 | Rolland et al. |
| 2004/0054286 A1 | 3/2004 | Audain et al. |
| 2004/0076545 A1 | 4/2004 | Watari et al. |
| 2004/0264293 A1 | 12/2004 | Laugharn et al. |
| 2005/0142664 A1 | 6/2005 | Loney |
| 2005/0150830 A1 | 7/2005 | Laugharn, Jr. et al. |
| 2005/0235740 A1 | 10/2005 | Desie et al. |
| 2006/0029525 A1 | 2/2006 | Laugharn et al. |
| 2006/0158956 A1 | 7/2006 | Laugharn, Jr. et al. |
| 2007/0053795 A1 | 3/2007 | Laugharn et al. |
| 2008/0031094 A1 | 2/2008 | Laugharn et al. |
| 2008/0050289 A1 | 2/2008 | Laugharn et al. |
| 2008/0056960 A1 | 3/2008 | Laugharn et al. |

FOREIGN PATENT DOCUMENTS

| | | |
|---|---|---|
| DE | 195 34 955 A1 | 3/1996 |
| DE | 19617924 | 11/1997 |
| DE | 19756874 A1 | 6/1999 |
| DE | 198 20 466 A1 | 11/1999 |
| DE | 103 25 307 B3 | 7/2004 |
| EP | 0643982 | 3/1995 |
| EP | 0709136 B1 | 1/1996 |
| EP | 0707892 B1 | 4/1996 |
| EP | 1128185 | 8/2001 |
| EP | 1344562 | 9/2003 |
| GB | 1105962 | 3/1968 |
| GB | 1536693 | 12/1978 |
| WO | WO 9502456 A1 | 1/1995 |
| WO | WO-98/58417 | 12/1998 |
| WO | WO 0025125 A1 | 5/2000 |
| WO | WO-2006033307 | 3/2006 |
| WO | WO-2007016605 | 2/2007 |

OTHER PUBLICATIONS

"Early experience with high-intensity focused ultrasound for the treatment of benign prostatic hypertrophy", Sullivan et al, British Journal of Urology, vol. 79 pp. 172-176, dated 1997.

"A prototype of a 500kHz ultrasonic Matricidal Device: Beam Scanner, Application to in-vivo heel bone quantitative characterization", Defontaine et al, 1999 IEEE Ultrasonics Symposium, pp. 1585-1588, dated 1999.

"A new method for the generation and use of focused ultrasound in experimental biology", as submitted on Jul. 6, 1942, Lynn et al., The Journal of General Physiology, vol. 26, The Rockefeller University Press, pp. 179-193, copyright 1942.

"Some applications of Ultrasonics", Brockelsby, J. Sci. Instrum., vol. 40, pp. 153-156, dated 1963.

Steven V. Ley and Caroline M. R. Low, Ultrasound in Synthesis, Springer-Verlag 1989, pp. 18-28.

European Search Report and Office Action from European Application No. EP 07 02 2472 dated Jan. 15, 2009.

International Search Report and Written Opinion from International Patent Application PCT/US2004/040133 dated Apr. 20, 2005.

* cited by examiner

METHODS AND SYSTEMS FOR PROCESSING SAMPLES USING ACOUSTIC ENERGY

CROSS-REFERENCE TO RELATED APPLICATONS

This application claims the benefit of U.S. Provisional Patent Application Ser. No. 60/704,794, filed on Aug. 1, 2005, and of U.S. Provisional Patent Application Ser. No. 60/715,660, filed on Sep. 9, 2005, the entire contents of which are incorporated herein in their entirety by reference.

FIELD OF THE INVENTION

The invention relates in general to treatment of materials by controlled acoustic energy, and more particularly to conditioning of such materials for subsequent analysis, processing and/or assays.

BACKGROUND OF THE INVENTION

Ultrasonics have been utilized for many years in a variety of diagnostic, therapeutic, and research purposes. Some uses of sonic or acoustic energy in materials processing include for breaking up and/or mixing of fluid suspensions of the materials being treated. Additional uses are in solubilizing or otherwise ensuring that all or substantially all of the constituents of a sample are in solution and/or in suspension. Regardless of the particular use, sample materials are typically contained in a plastic or glass enclosure, such as vials, tubes, culture plates/well, sample trays, or micro-titer plates, with the energy produced by an acoustic transducer coupled to the material in the enclosure by way of a coupling medium, such as water.

Micro-titer plates holding hundreds or even thousands of different samples have become widely used in research, development, and testing. The samples contained in the wells of the plates can be processed, for example mixed, individually or in groups, such as row-by row, by exposure to a focused acoustic beam. Acoustic mixing occurs by a number of processes, such as temperature, cavitation and acoustic streaming, and has been shown to improve antibody detection and reduce incubation times. However, most acoustic sample processing is still performed manually in small batches and processing parameters are determined empirically.

Accordingly, there is a need for acoustic systems and methods that provide automated, precise materials processing or reaction control, in particular for automated processing of large quantities of samples to be used, for example, in subsequent analytical processes and/or assays.

SUMMARY OF THE INVENTION

The invention addresses the deficiencies of the prior art by, in various embodiments, providing methods and systems for selectively exposing a sample or samples to controlled acoustic energy for the purpose of, for example, heating the sample, fluidizing the sample, mixing the sample, stirring the sample, comminuting the sample, disrupting the sample, enhancing a reaction in the sample, and sterilizing the sample. These are merely examples for the application of focused acoustic energy and not intended to be limiting.

Altering the characteristics of a sample in a controlled manner, especially biological and chemical samples, allows manipulation of the sample while preserving the viability, chemical and/or biological activity of the material as desired. For example, sample processing can be automated, with controls for at least one of acoustic energy location, pulse pattern, pulse intensity, and absorbed dose of the acoustic energy.

According to one aspect of the invention, an apparatus for processing a sample using acoustic energy includes an acoustic energy source for emitting acoustic energy substantially converging in a focal zone proximate to the sample, a medium for coupling the converged acoustic energy to the sample, a sensor for sensing a physical parameter of the sample, and a controller for controlling delivery of the acoustic energy to the sample based on a signal sensed by the sensor.

According to another aspect of the invention, in a method of processing sample arrays using acoustic energy, the method includes the steps of interrogating at least one sample to measure a status of the sample, coupling a transducer of focused acoustic energy to at least one sample, executing a processing sequence appropriate to that status to deliver acoustic energy to the at least one sample, periodically or continuously interrogating the at least one sample to detect the presence or absence of a desired condition of the at least one sample, and adjusting or terminating the processing sequence when the desired condition is detected.

According to yet another aspect of the invention, an apparatus for high-throughput processing samples using acoustic energy is provided which includes a first acoustic energy source for emitting acoustic energy substantially converging in a focal zone proximate to at least one sample, a medium for coupling the converged acoustic energy to the at least one sample for processing the sample, and a sensor for interrogating a sample to measure an initial status of the sample. Also provided is a controller for controlling delivery of the acoustic energy to the sample, wherein the controller executes a processing sequence appropriate to that status, periodically or continuously interrogates the sample to determine a desired outcome of the processing sequence, and adjusts or terminates the processing sequence when the processing sequence produces the desired outcome.

With the present invention, samples can be treated with acoustic energy when the samples are arranged in an array, for example, a micro-titer plate, and individual samples in the array may be treated differentially or identically. The treatment can be performed automatically under computer control. The acoustic energy can be applied uniformly across the array, or focused on a particular array element. The sample can be moved relative to the acoustic transducer in any or all of two or three dimensions. Alternatively, the acoustic transducer can be moved relative to the sample. The acoustic transducer can have one of several configurations. A single element transducer can be focused to a point as in the case of a spherically focused transducer or to a line as in the case of a cylindrically focused transducer. In addition, a multi-element transducer, as is well known in the medical diagnostic ultrasound field, can take the form of a one dimensional array wherein the focal beam can be steered in the plane of the elements to direct the focus by firing the individual elements at slightly different times. The focal beam of a two-dimensional array can be steered in the same way to direct the focus in three dimensions. The transducer may be focused by its inherent shape (i.e., concave spherical front face) or by means of an acoustic lens such as a silicone rubber lens on the front face of the transducer.

Vessels and sample receptacles arranged in the form of arrays may be permanently or temporarily sealed before acoustic processing, and hence can be sterile and contained throughout and after the acoustic treatment. Moreover, different samples in an array are prevented from contacting each other and/or coming into contact with the environment.

The exemplary systems and methods can record and store processing parameters associated with one or more samples. The processing parameters can subsequently be accessed for controlled delivery of acoustic energy in a manner preselected or customized for the sample. While in some embodiments, processing variables, such as energy delivered, frequency, intensity, duty cycle, burst pattern, cycles per burst, and pulse shape of the waveform, etc., may be subject to manual control, e.g., using knobs, dials, touch pads, sliders, or other manual input means, in other embodiments, some or all of the processing variables may be predetermined according to stored processing protocols. Such processing protocols may be semi-automatic, in the sense that the user may manually select a particular stored protocol, e.g., to select among protocols designed for particular purposes, such as dissolving chemicals, lysing cells, sterilizing biological samples, mixing liquids, etc. In other embodiments, the processing protocols may be fully automatic, in the sense that the acoustic processing system automatically selects a stored protocol upon detecting sample characteristics using sensors or other interrogation systems. The protocol may also be stored on a removable memory device, such as a CD-ROM, flash memory and the like.

For example, the acoustic energy delivered to the sample may be adjusted by the controller according to the volume of the sample, the sample temperature, and/or based on the type or concentration of particulate matter in the sample, for the purpose of, for example, comminuting the particles. The sensors may include temperature sensors, pressure sensors, optical sensors, such as infrared sensor, microscopes and/or video cameras, lasers, acoustic sensors such as electromagnetic or piezoelectric sensors, or a combination of such sensors. The sensors may be arranged coaxially and at an angle to each other.

The sensors may be employed for measuring a physical characteristic of one or more samples before, during and/or following acoustic treatment of the samples. The results of the measured characteristic can be stored for use in subsequent processing steps or to compile a treatment history for the sample(s). For example, samples may be selected for further processing or interchanged for other samples based on their previously measured characteristics, or samples may be grouped and/or classified based on treatment history. Similarly, a characteristic measured post-treatment can be assessed by itself or can be compared to the characteristic measured pre-treatment and used to determine whether a desired condition of the sample has been reached and/or to assign a subsequent treatment or processing step for the sample.

Exemplary samples include, without limitation, biological samples and chemical compounds. Samples may comprise one or more constituents such as, for example, solvents, reagents, nucleic acids, proteins, small organic or inorganic molecules, chemical compounds, or pharmaceutical or biopharmaceutical agents.

Exemplary sample vials include, without limitation, tubes, dram vials, culture wells, and micro-titer plates of varying configurations. The samples may include an identification marker, such as a barcode, logo, an RFID tag for tracking processing of the sample, and may also include a keying feature disposed on the apparatus for preventing insertion of the sample in the apparatus with a wrong orientation, or insertion of an inappropriate sample.

The samples may be coupled to the acoustic energy source by a liquid, semi-solid or solid medium. For example, the acoustic transducer may be placed in a tray surrounded by a fluid with a high transmissivity for the acoustic energy, and the semi-solid or solid layer may be placed between the fluid and the sample to prevent direct contact between the sample and the fluid. The semi-solid or solid layer may be made of silicone gel, elastomeric polyurethane, thermoplastic elastomer and the like, and may also have an additional cover layer to further protect the sample from contamination. Pressure may be applied to the sample or to the medium transmitting the acoustic energy, for example, by pressurizing the fluid, to improve acoustic coupling between the acoustic energy source and the sample.

Exemplary applications of the systems of the present invention are in the pharmaceutical industry where acoustic energy can be used to ensure that samples of chemical compounds or biological samples are in a substantially homogeneous solution or substantially uniform suspension prior to further chemical or biological testing. Further applications of the systems of the present invention are in the biotechnology industry where acoustic energy can be used to facilitate reactions involving nucleic acid hybridization, ligand-receptor binding, enzyme reaction, and the like. Further applications of the systems of the present inventions are in the diagnostic industry where acoustic energy can be used to facilitate reactions involving nucleic acid hybridization, ligand-receptor binding, enzyme reactions, and the like. Further features and advantages of the invention will be apparent from the following description of illustrative embodiments.

BRIEF DESCRIPTION OF THE DRAWINGS

These and other features and advantages of the invention will be more fully understood by the following illustrative description with reference to the appended drawings, in which like elements are labeled with like reference designations and which may not be to scale.

DETAILED DESCRIPTION OF CERTAIN ILLUSTRATED EMBODIMENTS

Figure 1:
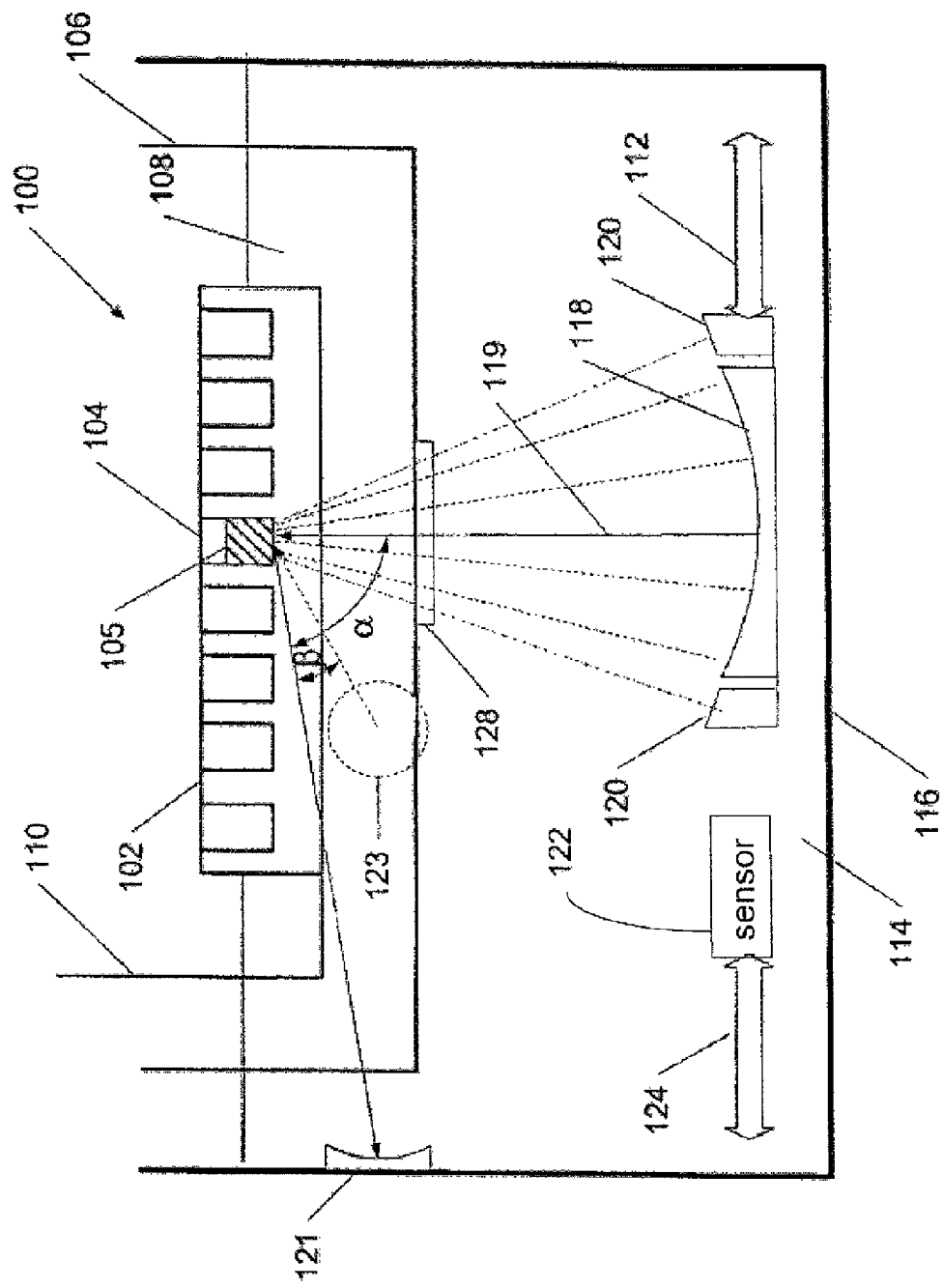
FIG. 1 is a first embodiment of an acoustic treatment apparatus with an exemplary sample tray exposed to focused acoustic energy according to the invention.

The invention, in various embodiments, provides systems, methods and devices for focused acoustic treatment of samples, and more particularly for controlled automated acoustic treatment of samples contained in vials or in wells of sample trays, such as micro-titer plates, for subsequent automated processing and/or assays.

The term "acoustic energy" used herein refers to acoustic energy, acoustic waves, acoustic pulses, including forms of ultrasonic energy and/or shock waves. As used herein, acoustic energy refers to the focused, high frequency (e.g., typically 100 kHz-100 MHz; greater than 500 kHz; greater than or approximately equal to 1 MHz; etc.), short wavelength (e.g., approximately 1.5 mm at a frequency of 1 MHz in water) acoustic energy. In contrast to the acoustic energy used in the methods of the present invention, sonication is generally used in the art to refer to the application of unfocused, relatively low frequency (typically 15-20 kHz), long wavelength (7-10 cm) energy used for material conditioning and/or processing.

Sample trays, micro-titer plates, and micro-well plates refer to plates having one or more wells in which individual samples can be deposited. These wells can be arranged in the form of a regular or irregular array.

Sensors can be used prior to, during, or after the acoustic treatment to analyze the samples, for example, by measuring responses to electromagnetic stimulation, such as optical spectroscopy, energy dispersion, scattering absorption, and/or fluorescence emission. Other measurable variables can include electromagnetic properties, such as electrical conductivity, capacitance or inductivity, as well as other physical parameters, such as sample uniformity, pattern analysis, and progression of uniformity across the samples or assemblies of samples, such as samples in the wells of micro-titer plates.

The use of acoustic mixing provides particular advantages for multiple samples arranged in an array, such as a micro-titer plate. This is particularly true when the sample and an analytical agent have different densities because in small-size containers or vessels, such as 384 or 1536 well plates, little mixing occurs when a low density fluid (e.g., with a density of approximately 1 g/cm$^3$) is layered over a higher-density reagent mixture. The location of the applied acoustic energy can be varied during treatment, e.g., stepped or dithered, and progress of the intermixing can be measured in situ. This is especially beneficial for removing bubbles from small volumes of fluid wherein surface tension effects are more significant than gravitational effects, or to lower the bubble content of fluids for reaction and/or analysis in volumes which are too low for turbulent mixing. Very small fluid volumes, as in high-density micro-titer plates (e.g., 1,536 wells per plate with 4 microliters per well), are not effectively mixed by shaking or vortexing. Acoustic treatment causes mixing in these small volumes by direct acoustic effects such as the action of acoustic pressure gradients on the fluid or by secondary effects such as the shear stresses induced by acoustically driven cavitation in the fluid.

FIG. 1 shows an exemplary embodiment of a system 100 for applying focused acoustic energy. In particular, the system 100 includes a sample holding tray 102 which in this embodiment is depicted as a sample tray 102. FIG. 1 further depicts sample 104, a sample tank 106, a coupling fluid 108, and a mechanism 110 for manipulating the tray 102, which will be described in more detail below. The top surface of the sample 104 forms a meniscus 105 between the sample material, for example, a liquid or viscous material, which may or may not contain particulates, and the environment, such as air. An outer tray or sample tank 106 made of an insulating material, such as rigid polystyrene foam, is set within a larger fluid bath 114 (e.g., water) in a transducer tank 116. The inner tray 106 may have heat-exchanger tubes or other heating or cooling devices within it (not shown) to allow a fluid 108, such as ethylene glycol or propylene glycol, in the tray 106 to be heated or cooled, relative to the fluid 114 in the outer bath of transducer tank 116. The fluids 108 and 114 in the inner and outer tray 106, 116, respectively, provide efficient transfer of the acoustic energy. The inner tray 106 has an acoustic window 128 disposed in the bottom. The acoustic window 128 is provided to improve impedance matching between the inner sample tray 106 and the fluids 108, 114, having an acoustic impedance similar to that of fluids 108, 114, and may be made of a thin film material having high acoustic transmissivity. This inner tray 106 is arranged so that the acoustic window 128 is aligned with an acoustic energy source/transducer 118 located outside the tray 106. The transducer 118 can be supported in the tray 116 by a suitable mechanism (not shown) to allow movement of the transducer 118 relative to the tray 116 in one or more directions, for example, in three dimensions, as indicated schematically for one direction by arrow 112. According to one embodiment, the transducer 118 can be a spherically focused transducer that generates a substantially coaxial acoustic field, for example, a 70 mm diameter transducer having a focal length of, for example, 63 mm, which generates an ellipsoidal focal zone approximately 2 mm in diameter and 6 mm in axial length when operated at a frequency of about 1 MHz. In another embodiment, the transducer 118 can be a line source that produces a substantially parallel acoustic field, e.g., a 35 mm long, or even 100 mm long transducer, that can simultaneously affect multiple samples arranged in a linear array. In certain embodiments, a subject system may employ multiple transducers (whether linear or, preferably, spherical in configuration) to simultaneously treat multiple samples in a sample array with individualized protocols, e.g., protocols tailored to the identity or characteristics of each sample, such as will be discussed in greater detail below. The multiple transducers may be an array of transducers, e.g., disposed to align with samples in a multi-sample array, or may be two or more independently positionable transducers that can be moved to align with particular samples of a multi-sample array. The transducer 118 can be positioned so that the focal zone is proximate the surface of the fluid bath 108. The transducer 118 can be driven by an alternating voltage electrical RF-frequency signal generated electronically by a control system, such as control system 400 described in FIG. 4.

Also placed in the tank 116 at any suitable location may be one or more detectors/sensors 120, 122 capable of detecting certain physical properties of the sample before, during, and/or after acoustic processing. Exemplary detector may include an additional acoustic transducer 120 suitable to transmit and/or receive an acoustic interrogation beam which can be used to assess one or more characteristics, such as the fill level, temperature, cavitation, volume, homogeneity, etc., of a sample 104 located within a micro-titer plate or sample tray 102. The sample holding tray 102 in the depicted example is attached to a holder, schematically shown with the reference symbol 110, which in certain embodiments is attached to actuators (not shown) to allow movement of the vessel 102 in at least one direction in a XYZ coordinate system. The system may include other types of sensors, such as optical sensors, for example Infrared (IR) temperature sensors, laser scattering sensors, video monitoring devices and the like, schematically shown with the reference symbol 122, to measure other physical sample properties affecting acoustic sample processing. Like transducer 118, sensor 122 may also be movable in outer tray 116 relative to the position of sample 104 to allow, for example, focusing of an optical sensor 122.

The arrangement with two containers 106, 116 permits the use of separate fluids and substantially independent control of the temperature of the inner and outer treatment baths 108, 114. The smaller volume of the inner tray 106 facilitates the use of antifreeze mixtures, such as a mixture of propylene glycol and water, at temperatures below the freezing temperature of water. This, in turn, allows samples 104 to be processed and treated at temperatures below the freezing temperature of water. This embodiment is beneficial for treatment applications requiring that the sample materials 104 be maintained at temperatures near or below the freezing point of water. It allows for the containment of treatment bath fluids 108, such as antifreeze solutions, that may not be compatible with the transducer 118 and other system components, such as sensors 120, 122. It also allows the transducer 118 to be maintained at a different temperature than the samples 104. It will be understood by those skilled in the art that the roles of acoustic transducer 118 and acoustic sensor 120 can be reversed in that sensor 120 may operate to emit the acoustic processing beam while transducer 118 performs sensing functions.

Figure 2:
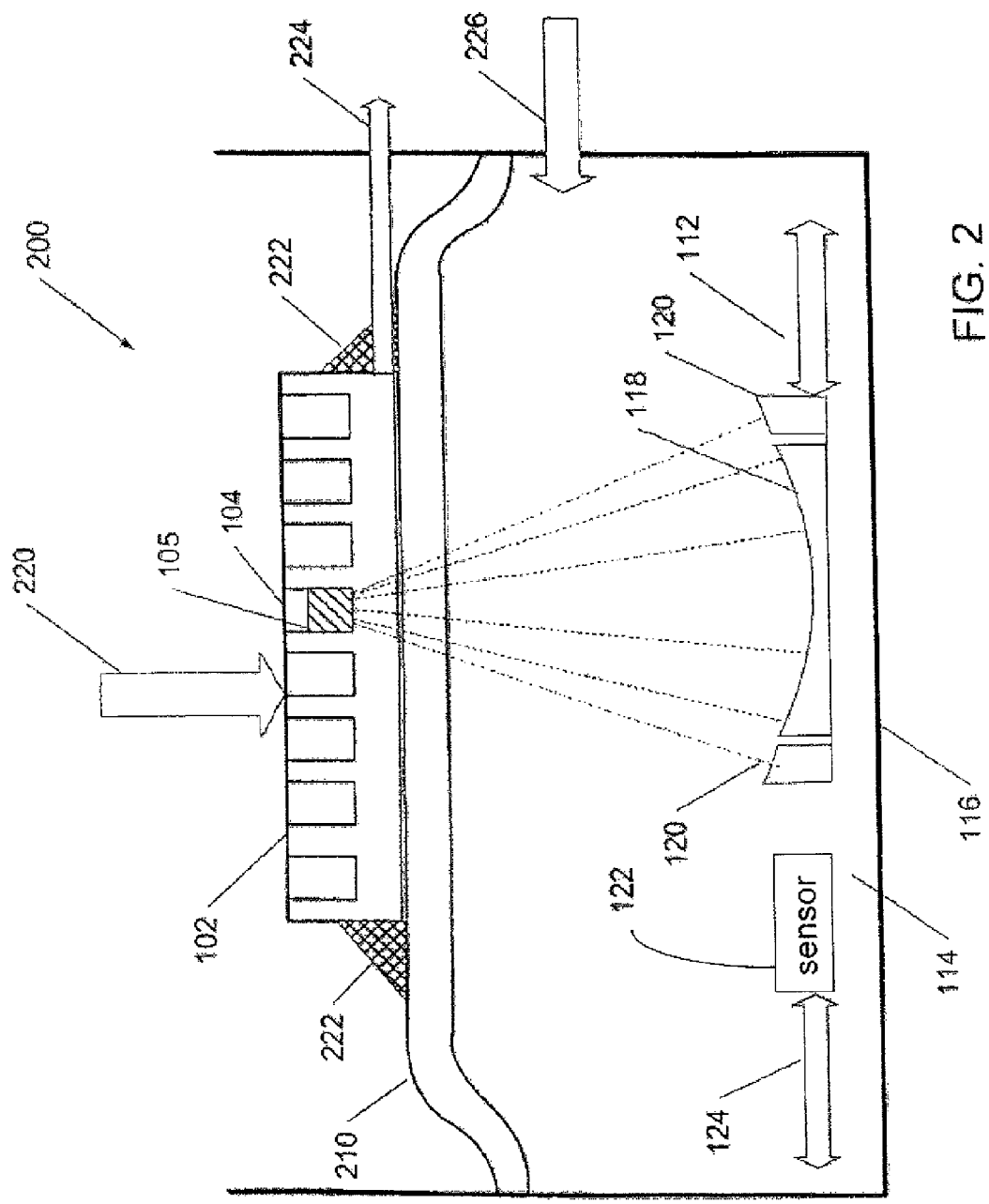
FIG. 2 is a second embodiment of an acoustic treatment apparatus with an exemplary sample tray exposed to focused acoustic energy according to the invention.

FIG. 2 shows another embodiment of a system 200 for applying focused acoustic energy to a sample located in a sample tray 102. Unlike in the system 100 of FIG. 1 where the acoustic energy is transmitted to the sample through the inner bath 108, the acoustic energy is transmitted in the depicted system 200 through a solid or semi-solid layer 210 of, for example, silicone gel, elastomeric polyurethane or thermoplastic elastomer. Exemplary suitable sound-transmitting media are listed in Table 1. This list, however, should not be viewed as comprehensive and exhaustive, and other acoustic coupling media with adequate sound transmission properties may be used instead. Layer 210 may optionally be sealed by an impervious membrane such as, for example, a plastic sheet or film, to prevent direct contact between the layer 210 and the sample or sample tray 102. This arrangement can provide temporary seating of the sample on the transducer, and different end effectors can be placed on the sound transducer to optimize transmission of acoustic energy. In this arrangement, the sample tray 102 may be pressed against the layer 210 for more efficient transfer of acoustic energy, as indicated by arrow 212. For enhanced contact between micro-titer plate 102 and layer 210, a sealing means 222 may be disposed around the periphery of sample tray 102, with the space between sample tray 102 and the top surface of layer 210 being connected to a vacuum source 224 to remove any gas residue and/or bubbles remaining between sample tray 102 and layer 210. Layer 210 may be free-floating on the fluid surface of bath 114 or may be suitably supported in other ways, such as by making the membrane of laminate 210 facing the bath 114 more rigid, by a lattice frame (not shown) or the like. The system 200 thereby allows "dry" processing of sample tray 102 and/or sample 104 by preventing direct contact between sample tray 102 and/or sample 104 and a fluid bath, such as bath 108. Alternatively, bath 114 may be pressurized by, for example, a source 226 of compressed gas or air from, for example, a bladder or piston (not shown) to distend layer 210 and enhance acoustic contact with sample tray 102. Care should be exercised so as not to form a gas or air layer or bubbles in the fluid bath 114 which could disrupt efficient energy delivery from the acoustic energy 118 source to the sample 104. Acoustic contact may also be enhanced by disposing a liquid or gel acoustic couplant, such as is typically used in the medical diagnostic ultrasound field, at the interface between sample tray 102 and layer 210, although this is less desirable than a truly "dry" system wherein no liquid or gel residue comes in contact with sample tray 102 during processing and/or remains on the sample tray 102 after processing.

Table 1 below lists the relative acoustic transmission of various materials relative to water (100%):

TABLE 1

| Material | Thickness (in mm) | Transmission at 1 MHz (in % relative to water) |
| --- | --- | --- |
| No material (water) | | 100 |
| Acetate | 0.13 | 80 |
| Latex | 0.10 | 50 |
| PET (Mylar) | 0.13 | 90 |
| Silicone | 0.13 | 95 |
| PET (Mylar) | 0.05 | >95 |

As mentioned above, the acoustic treatment systems may include one or more sensors, such as exemplary sensors 120, 122, for monitoring the energy or its effect. The sensor signals can be employed in a feedback mechanism coupled with the source of acoustic energy to regulate the energy (for example, voltage, frequency, pattern) for transmitting acoustic energy to a target. For example, as discussed above, input from the sensors may be used to assess whether treatment is needed or to select a treatment protocol for processing a sample. Similarly, sensors may be used during processing for monitoring the sample temperature, cavitation, homogeneity (e.g., presence or absence of particulate matter in the solvent, and/or the size of such particles), and sample volume, to name a few. Details of sensor applications in acoustic processing are described, for example, in commonly assigned U.S. Pat. No. 6,948,843, the entire contents of which are incorporated herein by reference. As mentioned above, the roles of transducer 118 and sensor 120 can be reversed.

Interfaces, such as an interface between air and water, cause reflection of an incident ultrasound field. While reflection should be minimized for transmitting acoustic energy to the sample, a signal emitted from the transducer 118 or from a separate interrogation transducer/sensor 120 and reflected by an interface, such as the meniscus of sample 104 in sample tray 102, can be used to quantify the height and therefore also the volume of the sample. In one embodiment, sensor 120 may be implemented as an acoustic transducer and emit a short burst of acoustic energy with a duration of 1 ms or less for interrogating the sample. Such short burst is also referred to as a "ping." As mentioned above, the interrogation burst can be focused on a sample, such as sample 104. Due to reflection at the various interfaces encountered by the propagating interrogation sound wave, the sensor 120 receives a return signal after a transit time corresponding to twice the distance between the sensor 120 and the respective interface. For example, it takes a sound wave approximately 10 ms to travel a distance of 1 cm, which is easily resolved by a detection system. The location of the meniscus of the sample 104 in a well can then be determined from the arrival time difference between the sound wave reflected at the bottom of the sample, such as sample tray 102, and the reflection at the liquid-air interface at the meniscus.

The volume of the sample can be taken into consideration when applying acoustic energy for treatment of the sample, as will be described in more detail below.

Likewise, air bubbles and particulates can also block or reflect energy transmission through the sample volume. The same principle described above for determining the position of the meniscus can therefore also be used to evaluate the sample volume for the presence or absence of particles, and/or the size and/or the quantity of such particles.

Figure 9:
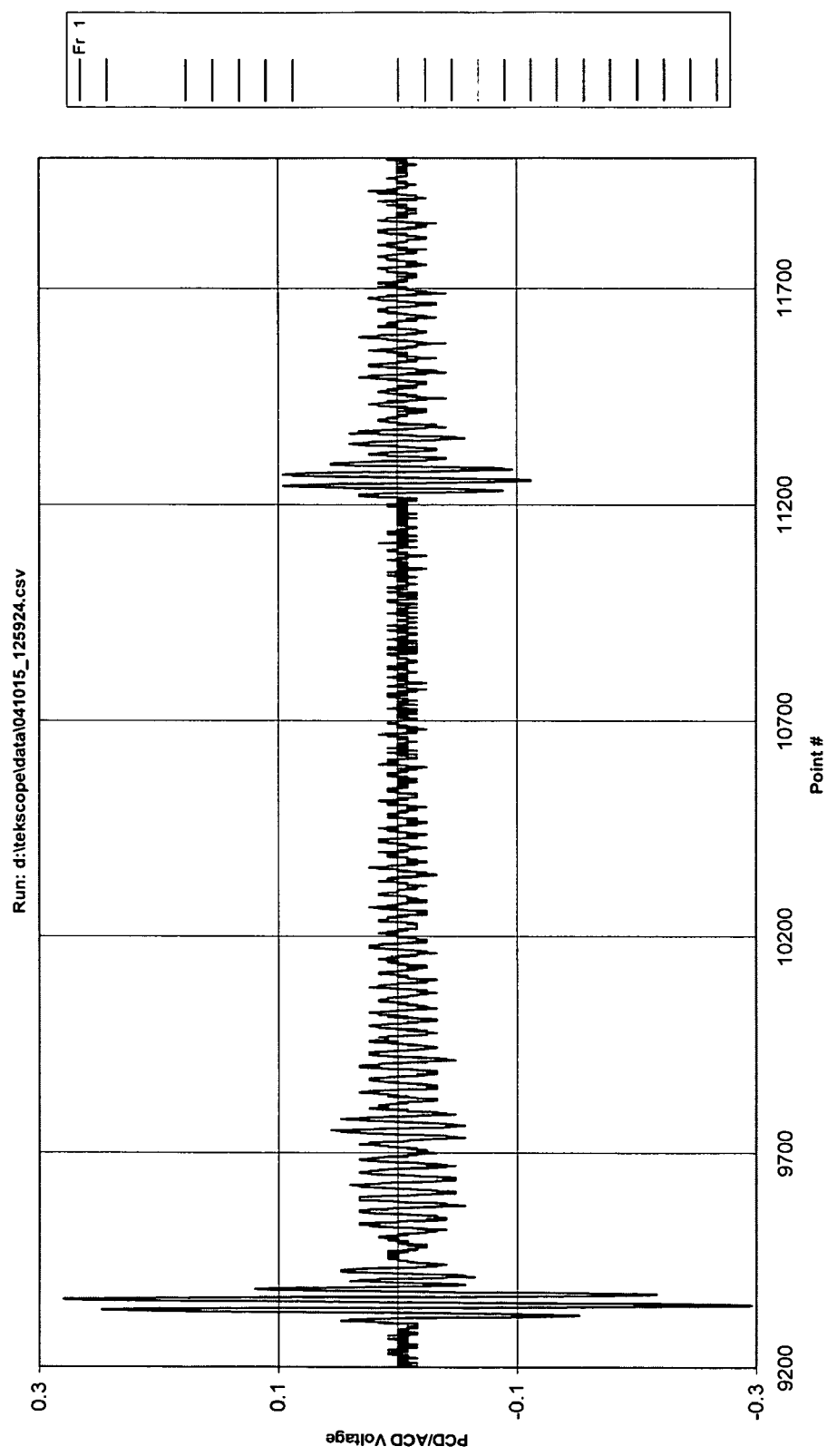
FIGS. 9 and 10 show detection of the presence of particles ($YO_x$) by reflection pinging.

Pinging can therefore also be used to determine the presence of particles in a sample, such as $YO_x$ which is insoluble in water. Briefly, a sample vessel containing water and 10 mg of $YO_x$ was thoroughly mixed and analyzed using reflection pinging. Referring now to FIG. 9, a strong signal was detected in the thoroughly mixed solution (note the signal at approximately 11200). This strong signal indicates that reflection pinging is sufficiently sensitive to detect the presence of undissolved material (e.g., $YO_x$) that is suspended within a sample.

Figure 10:
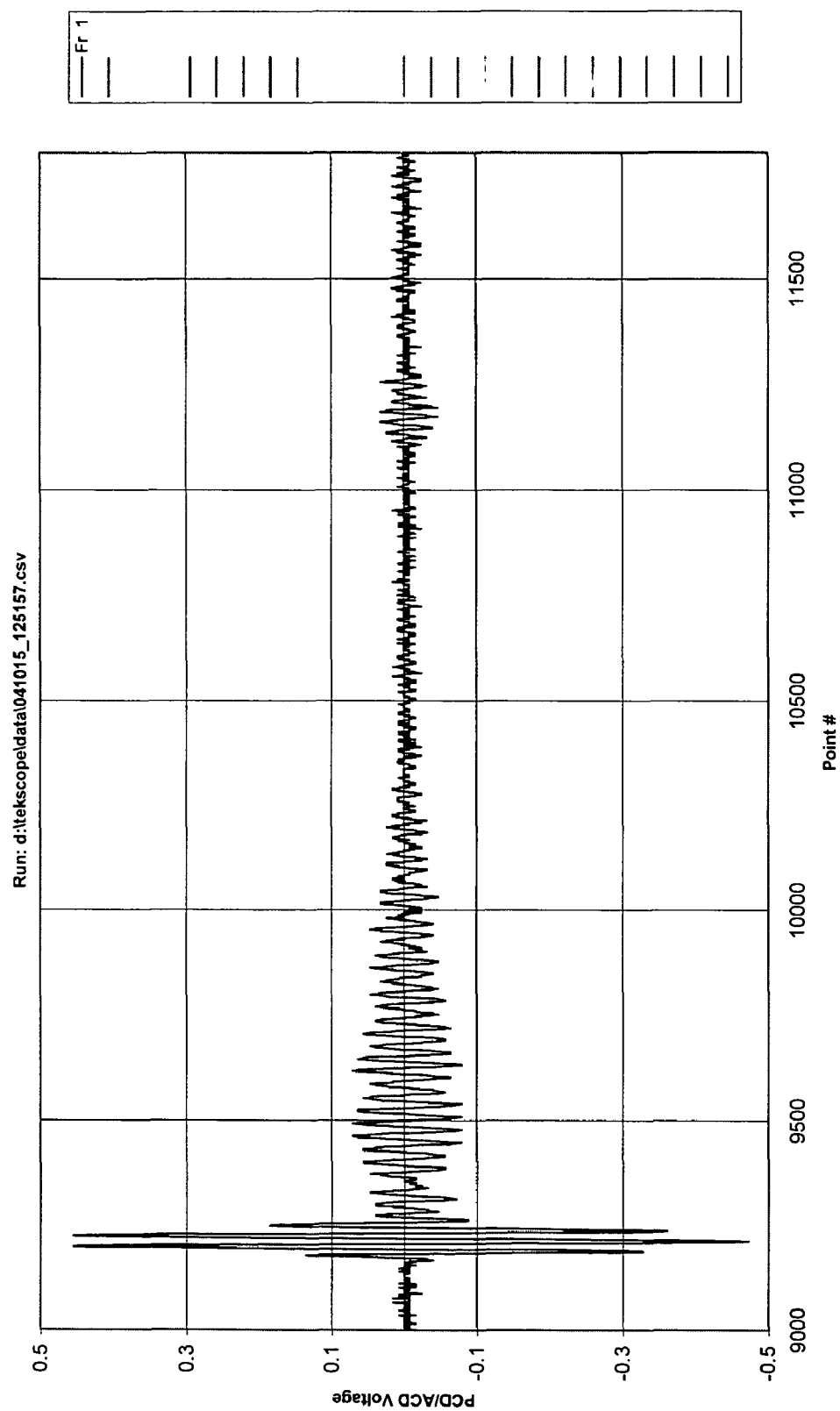

FIG. 10 shows that the strong signal observed when the $YO_x$/water solution was thoroughly mixed decreases when the $YO_x$ is allowed to settle to the bottom of the surface of the reaction vessel (note the reduced signal strength at approximately 11200 in comparison to FIG. 9).

Figure 3:
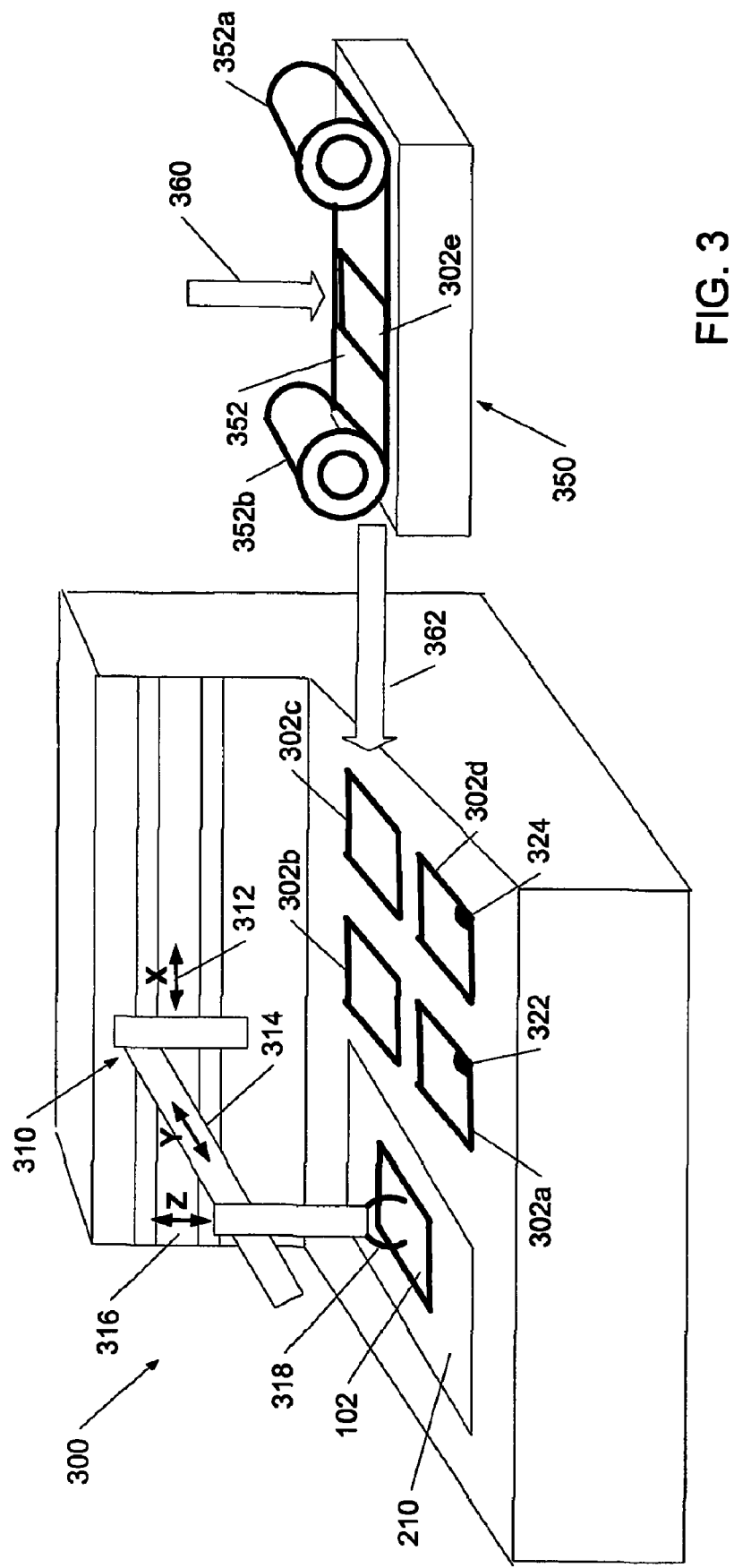
FIG. 3 is an exemplary embodiment of a high throughput acoustic treatment apparatus with a connected sealing station according to the invention.

FIG. 3 shows an exemplary processing station 300 for acoustic treatment of a sample (not shown) placed on a sample tray 102 or in another vessel, such as a vial, as shown in more detail in FIGS. 1 and 2. The station 300 includes the transducers, sensors, detectors, actuators shown in FIGS. 1 and 2, which are obscured from view by the housing. The sample tray 102 may rest, for example, on the membrane or laminate 210 described above with reference to FIG. 2. An X-Y-Z positioning system 310 implemented, for example, as a cantilevered beam structure 310 enables a sample holder, such as a gripping device 318, to move in three—preferably orthogonal—directions as indicated by arrows 312, 314, and 316. In addition, the positioning system 310 may also allow the sample to rotate and/or tilt. Other types of sample holder, operated mechanically, electro-magnetically or by suction may be employed instead of or in addition to the gripping device 318 for picking sample vessels 102, 302a, 302b, 302c, 302d. The sample vessels 302a, 302b, 302c, 302d may be picked up and transported by the X-Y-Z positioning system 310 to the location of sample vessel 102 in any order. Sample holder 310 may also be configured to apply the pressing force 220 (FIG. 2) to press plate 102 against the membrane 210 for efficient coupling to the acoustic transducer.

Sample 104 (FIGS. 1 and 2) may initially be open at one end, but may be sealed prior to processing to prevent spillage and/or (cross-)contamination. As shown in FIG. 3, processing station 300 may be operatively connected to a sealing station 350 placed upstream of the processing station 300, with a sealed sample tray or micro-titer plate 302e transported in the direction of arrow 362. For example, a sheet of flexible metal or plastic foil, film, or wrap, such as Parafilm™ or Teflon™ tape, can optionally be placed in contact with or affixed to the plate to prevent cross-contamination between contents of the wells, or between the wells and the source of acoustic energy and/or the environment. In certain embodiments, it may be advantageous to select a sealing material that will not interact with the sample in such a way as to contaminate it, e.g., by degrading or leaching substances such as plasticizers into the sample. In one exemplary embodiment for sealing sample trays 302e, the sealing station 350 may include a roll 352a of a plastic film material 352, such as Mylar, that can be pressed against the top surface of plate 302e by applying pressure, as indicated by arrow 360, and then cut to size (not shown). Any remaining unused section of the film could then be wound up on roll 352b. It would, of course, also be possible to precut the film material, or to use plugs, and the like, which may be applied to the sample trays 302e by a different suitably configured sealing station. Alternatively, the plates 102 may be supplied to processing station 300 presealed, thereby obviating the need for a connected sealing station 350, or temporary sealing may be incorporated into the processing apparatus, as discussed below for the clamshell design.

Figure 4:
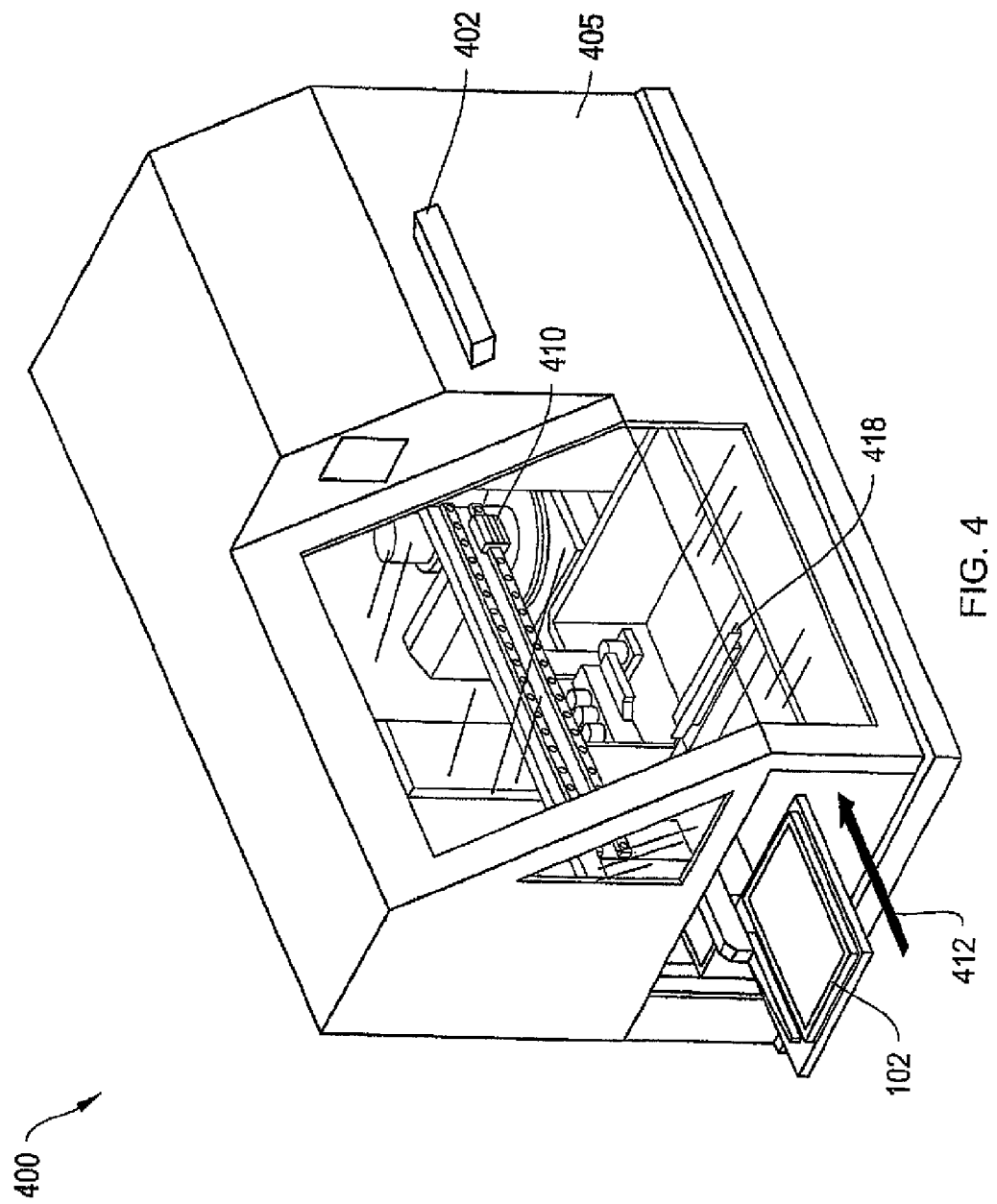
FIG. 4 is another exemplary embodiment of a high throughput acoustic treatment apparatus according to the invention.

Referring now to FIG. 4, a positioning system 400 is adapted to function with the particular configuration of the acoustic processing apparatus, and may be integral to the apparatus or substantially external to the acoustic processing apparatus.

For example, the acoustic processing apparatus can be configured as a box 405 or tube open on one end or on opposite ends, e.g., so that samples to be processed enter from one end, and processed samples exit from the other end. In on such embodiment (not shown), the positioning system (or separate positioning systems located at each end), such as a robotic arm, may be substantially external to the acoustic processing apparatus, and may place untreated samples 104 disposed in sample holding tray 102 in a location where the component samples are in an acoustic coupling relationship with the acoustic energy source 118 from one end, and remove treated sample holding tray 102 from the other end after processing.

Alternatively, in another exemplary embodiment depicted in FIG. 4, the positioning system 410 is integral to the apparatus. The positioning system 410 may move a sample holding tray 102 from an initial loading position into an acoustic coupling relationship with the acoustic energy source 418 shown here as a linear source, and optionally then move the sample holding tray 102 into a position suitable for removal from the apparatus. In such embodiments, a second, external positioning system, such as robotic arms as mentioned above, may be used to move samples from an initial location, such as a first storage location, into an operative relationship with the integral positioning system, and/or to return treated samples to a final location, which may be the same or a second storage location.

An integral positioning system 410 is preferably configured so as not to interfere with the acoustic coupling process, but otherwise may take any of a number of forms. For example, one suitable conveyor system might be a thin plastic film or sheet that functions as a conveyor belt. Alternatively, the positioning system may take the form of parallel tracks or slots adapted to retain opposing sides of a sample holding tray 102. The tracks or slots may be fitted with rollers or gears that interact with the sample holding tray 102 to propel the sample holding tray 102 along the track and through the acoustic processing system. Yet a third type of integral positioning system, such as the exemplary system 400, grasps sample holding tray 102, e.g., by clamping sample holding tray 102 at one or both sides, carries sample holding tray 102 into an acoustic coupling relationship with the acoustic energy source 418 as indicated by arrow 412 (and, for embodiments wherein the acoustic coupling medium is a solid or semi-solid medium, such as a silicone pad, may further press the samples against the acoustic coupling medium) and, after processing, may return the sample holding tray 102 to the same side or may carry the sample holding tray 102 to the other side of the acoustic processing system 400.

Figure 5:
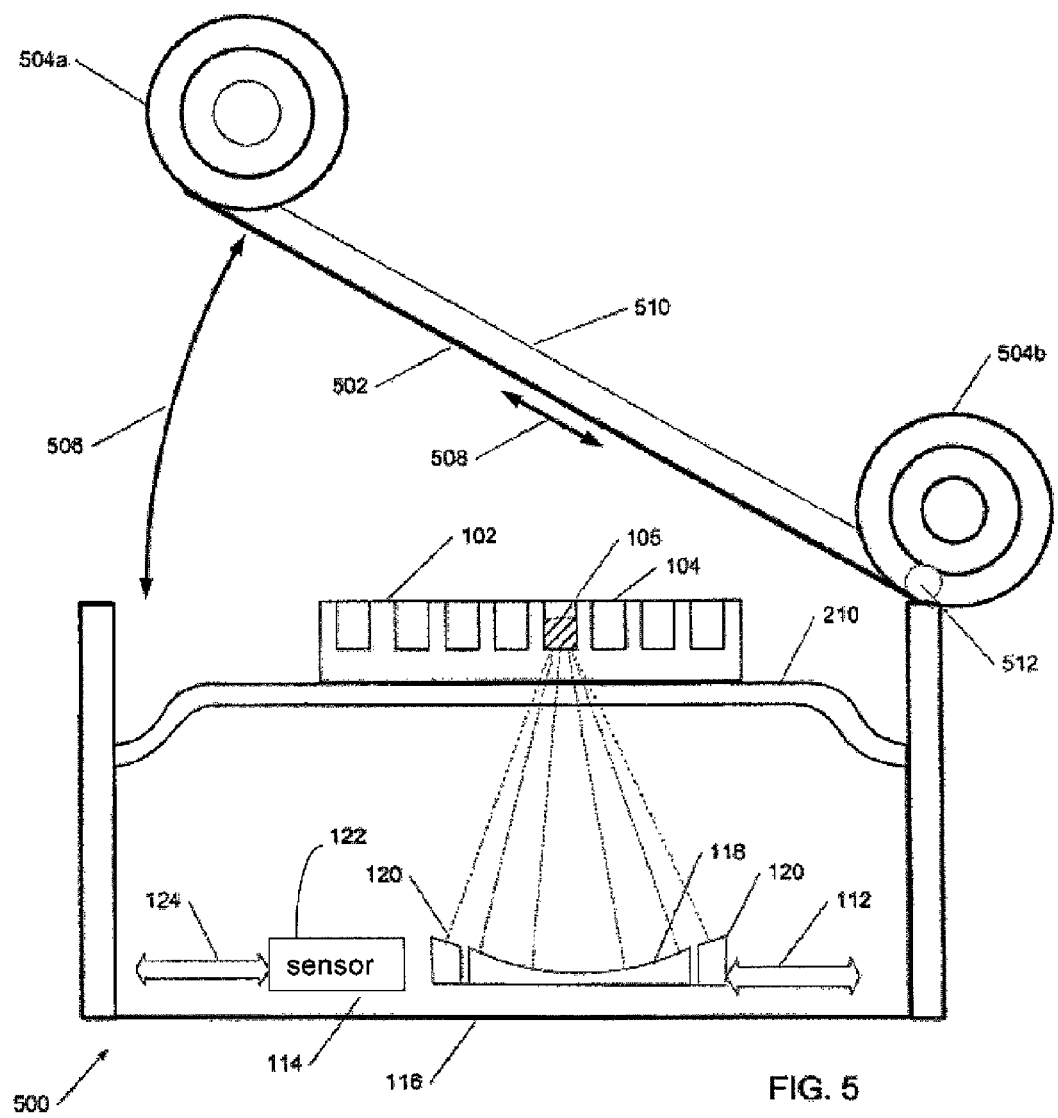
FIG. 5 is an exemplary embodiment of a clam-shell design of an acoustic treatment apparatus with an integrated sealing station according to the invention.

In yet another embodiment depicted in FIG. 5, an acoustic processing system 500 has a movable lid or cover 510, such that when the lid or cover 510 is in the illustrated open position, a sample 102 can be placed in the apparatus by a positioning system (not shown in FIG. 5). The lid or cover 510 is then closed, as indicated by arrow 506, and treatment of the samples 104 can occur. The lid or cover 510 may be configured to cover one or more faces of the acoustic processing system, e.g., it can include only the top face of a box-shaped housing, or the top face and one or more sides. The lid or cover 510 may move in any suitable way, for example, by sliding to one side or by rotating on a hinge 512 or lever arm (e.g., a "clamshell" design).

In one embodiment of a clamshell design, the cover is configured to press a sample 102 against a solid or semi-solid acoustic coupling medium 210. Thus, after sample tray 102 is placed in the open chamber, the lid 510 may swing closed and simultaneously exert pressure on the top of sample tray 102, pressing the bottom of vessel 102 against the acoustic coupling medium below. In certain embodiments, such a system can be employed with open-ended sample containers 104, such that the lid serves to cover the tops of the containers during processing.

To prevent contamination with previous samples, the lid 510 may be fitted with a plastic film 502 that contacts the tops of the sample containers 104. In certain such embodiments, the film 502 is configured to be replaced between successive treatments. For example, the film 502 may be carried on rollers 504a, 504b located to either side of the lid 510, one roller (504a or 504b) to supply clean film, and the other roller (504b or 504a) to collect used film. After each treatment, the rollers 504a, 504b operate to place clean film 502 in the appropriate position of the lid. As an additional measure to avoid contamination and to conserve samples, the system may be configured to move the film slightly after each treatment, as indicated by arrow 508, but before the lid is raised, such that any residual sample that may adhere to the film is effectively wiped on the top edges of the containers. In such embodiments, the film 502 may be configured to move enough to wipe as much of the film as possible without allowing a used portion of film to contact an adjacent sample as an additional precaution against cross-contamination of samples. Accordingly, for closely spaced samples, it may be advantageous for the film 502 to move back and forth, effectively wiping half of the cover film against one side of the sample vessel 104 and the other half of the cover film against the other side of the sample vessel 104 prior to opening of the lid 510 and disengagement of the film 502. Other methods of handling open-ended samples will be addressed below.

As described above, in certain embodiments, the positioning system may move the sample or array of samples relative to the transducer and the other parts of the apparatus, e.g., during acoustic processing of the samples. In alternative embodiments, the transducer is moved while the sample holder remains fixed relative to the other parts of the apparatus. As an alternative, movement along two of the axes, for example, X and Y, can be assigned to the sample holder whereas movement along the third axis, such as Z in this case, can be assigned to the transducer. The motion of the samples relative to the transducer can be smooth and continuous, or can occur in a stepwise fashion, e.g., the transducer and sample array remain stationary in a coupling relationship relative to one or more samples of the array until treatment of those samples is complete (e.g., as determined by sensor feedback), followed by movement to a position having a coupling relationship with one or more different samples, etc.

In one embodiment, any one of the positioning systems 310, 410 may include at least one motorized linear stage (not shown) that allows positioning of the sample. Referring back to FIG. 3, the positioning system 310 can move sample 102 during and as part of the treatment process and between processes, as when multiple samples or devices within the sample 102 are to be processed in an automated or high-throughput format. The positioning system 310 may position or move the sample 102 in a plane transverse to the focal axis of the acoustic energy source 118 (FIGS. 1 and 2; X-and Y-axes). The positioning system 310 can position and move the sample 102 along the focal axis of the acoustic energy source 118 and lift or lower the sample 102 from or into the fluid bath 108 (FIG. 1) or press the sample 102 against the membrane 210 (FIG. 2) (Z-axis). The positioning system 310 can also position the acoustic energy source 11-8 and any or all of the sensors 120, 122 in the fluid bath 114 along the focal axis of the acoustic energy source 118, if the sensors 120, 122 are not affixed in the water bath 114, as well as lift, lower, or otherwise move the acoustic energy source 118. The positioning system 310 also can be used to move other devices and equipment such as detection devices and heat exchange devices from or into the fluid bath 108, 114 (Z-axis). The three-axis positioning system enables automated energy focus adjustment in the Z-axis when used in conjunction with a sensor for measuring the ultrasound intensity at the sample or the energy absorbed by the sample. In one embodiment, a needle hydrophone can be mounted in a fixture on the sample positioning system. The hydrophone can traverse the focal region in three dimensions to record the acoustic intensity as a function of position to map out the focal zone.

A positioning system may further be adapted for selecting individual samples 104 from a stored library, arranging them in a sample holding tray 102, such as a rack or tray, for acoustic processing and optional further manipulation (such as removing aliquots for testing in an assay, etc.). In certain embodiments, such as where the positioning system includes robotic arms, this function can be carried out using the same components as discussed above; in other embodiments, additional elements, such as robotic arms, may be used in conjunction with positioning system elements discussed above.

Figure 6:
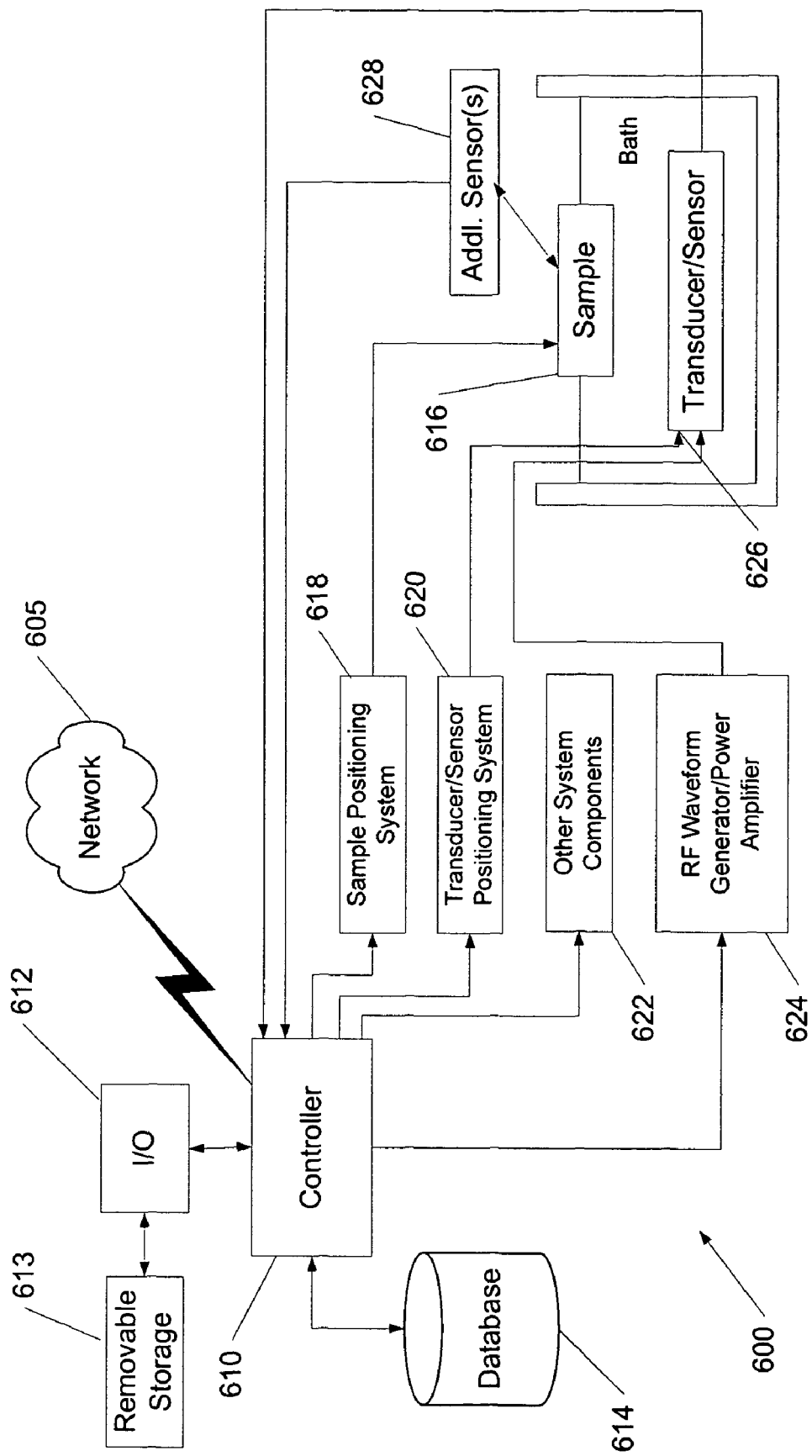
FIG. 6 is a schematic diagram of a controller for controlling an acoustic treatment apparatus according to the invention.

Referring now to FIG. 6, the processing stations 300, 600 depicted in FIGS. 3 and 4, respectively, and other system components, such as the sealing station 350 or the movement of film 502 (FIG. 5), can be controlled by a control system 600. Control system 600 includes a controller 610, which may be a general-purpose computer, a workstation or a dedicated industrial controller, which may be connected to an external terminal and/or other suitable hardware 612 for input and output of programming instructions and/or data. The controller 610 may be connected to a storage device 614 capable of storing programs, data and processing history of the acoustic treatment of samples 616. In this way, records can be maintained for all or selected samples for future analysis.

For example, storage device 614 may include a database of the identities, locations, and characteristics (such as volume, concentration, solvent, etc.) of a library of stored samples. The database may further be used to record subsequent events. For example, data collected by the acoustic processing system in a pre-treatment interrogation, such as volume, temperature, presence and/or amount of particulate matter, etc. This data can be used, for example, to determine whether solvent evaporation has taken place or whether a dissolved compound has fallen out of solution, or even to determine whether the sample matches the stored criteria, e.g., as a check to verify that the sample is the expected sample. Similarly, the database can be used to store information about the treatment protocol administered, such as the time, waveform, total energy, or other characteristics of the treatment, and can be used to store the results of a post-treatment interrogation, e.g., to record the absence of particulate matter, that the temperature has not exceeded a threshold level, etc. This information can be recorded over a number of treatment and storage periods, thereby storing a detailed history of a plurality of samples.

Storage device 614 may store one or more predetermined treatment protocols, e.g., a variety of treatment protocols specialized for particular purposes or for particular sample types. One of these protocols may be selected for a particular sample by an operator, by controller 610 in response to sensor feedback, or by a combination of controller 610 and an operator.

Treatment protocols and similar instructions for treating samples may also be stored on a removable storage component 613 of the control system 600. This may be useful for treatment protocols that are relatively specialized to specific uses, sample types, or objectives. The storage component 613 may be in the form of a memory card or flash drive that slides into a memory card slot 402 disposed on housing 405. The slot 402 may be arranged on any part of the treatment apparatus 400 or the controller 610, such as the I/O device 613, accessible to an operator. Other suitable interchangeable memory components include compact discs (CD), compact discs with read-only memory (CD-ROM), digital versatile discs (DVD), diskettes, and other suitable memory chips. In one embodiment, the treatment apparatus 400 or the controller 610 may be connected to a network 605, such as a LAN, WAN or the Internet, and capable of downloading treatments protocols from the respective network.

The controller 610 may also control one or more systems for positioning the sample 616 in the treatment bath (Sample Positioning System 618), for positioning the transducer or any movable sensors 626 in the treatment bath (Transducer/Sensor Positioning System 620), and for operating any other system components 622 of the acoustic sample processing system. The controller 610 receives feedback signals from the sensors 626 and any other sensor(s) 628 employed in the acoustic processing system for characterizing conditions of the sample(s) and/or the delivery of the acoustic energy to the sample(s). An RF waveform generator/amplifier 624 receives control signals from controller 610 and controls the delivery of RF power to the transducer/acoustic energy source 626. As discussed above, sensor feedback can be used to construct a treatment protocol for a particular sample, or to select a treatment protocol from among a set of protocols accessible to controller 610 (e.g., stored in storage device 614).

The control system 600 can generate a variety of useful alternating voltage waveforms to drive the acoustic transducer 626. For instance, a high power "treatment" interval consisting of about 5 to 1,000 sine waves, for example, at 1.1 MHz, may be followed by a low power "convection mixing" interval consisting of about 1,000 to 1,000,000 sine waves, for example, at the same frequency. "Dead times" or quiescent intervals of about 100 microseconds to 100 milliseconds, for example, may be programmed to occur between the treatment and convection mixing intervals. A combined waveform consisting of concatenated treatment intervals, convection mixing intervals, and dead time intervals may be defined by the operator or selected from a stored set of preprogrammed waveforms. The selected waveform may be repeated a specified number of times to achieve the desired treatment result.

Measurable or discernible process attributes such as sample temperature, water bath temperature, intensity of acoustic cavitation, or visible evidence of mixing in the sample processing vessel 102 (FIGS. 1 and 2), may be monitored by the sensors during processing and employed in a feedback loop of control system 600 to modify automatically the treatment waveform during the treatment process. This modification of the treatment waveform may be a proportional change to one or more of the waveform parameters or a substitution of one preprogrammed waveform for another. For instance, if the sample temperature deviates excessively during treatment from a set-point temperature due to absorbed acoustic energy, the control system 600 may proportionally shorten the treatment interval and lengthen the convection mixing interval in response to the error between the actual and target sample temperatures. Or, alternatively, the control system 600 may substitute one predetermined waveform for another. Changes in the waveform may include changes in frequency, intensity, duty cycle, burst pattern, cycles per burst, and pulse shape of the waveform. Certain treatment processes my apply a high power "treat" interval alternating with a low power "mix" interval, optionally separated by a dead time. The frequency and duration of these intervals may be the same or different. For example, bubble growth (cavitation) and collapse can be substantially avoided by limiting the number of cycles in each burst. In another embodiment, the delivered acoustic treatment power or energy may be adjusted depending on the actual volume of the sample which can be measured by one or more of the sensors. The control system 600 may be programmed to terminate a process when one or more of the sensors 626, 628 signal that the desired process result has been attained.

In one embodiment, frequency sweeping can be employed wherein the RF drive frequency of the acoustic transducer is modulated around the optimum operating frequency of the transducer with a frequency of at most $\pm \lambda/2$, where $\lambda$ is the acoustic wavelength in the transmission medium. The roundtrip path length and thus the number of fixed wavelengths in the round trip path would then continually vary, resulting in maximum power transfer at some locations, and in minimum power transfer at other locations. This would enable focusing the maximum acoustic energy precisely at the location of the sample with the need to mechanically move the sample relative to the transducer in the tray. In addition, frequency sweeping can also be used to deliver an average acoustic energy to the sample substantially independent on the precise sample position by "dithering" the transducer frequency.

The feedback control system 600 can include a variety of sensors, and a variety of sensed properties may be appropriate for providing input for feedback control. These properties can include sensing of temperature of the sample; sonic beam intensity; pressure; bath properties including temperature, salinity, and polarity; sample position; and optical or visual properties of the samples. These optical properties may include apparent color, emission, absorption, fluorescence, phosphorescence, scattering, particle size, laser/Doppler fluid and particle velocities, and effective viscosity. Sample integrity or comminution can be sensed with a pattern analysis of an optical signal. Any sensed property or combination thereof can serve as input into controller 610. The feedback can be used to control any output of the system, for example beam properties, sample position, and treatment duration.

For example, sensor 122 (see FIGS. 1 and 2) can be a camera capable of being focused on one or more of the samples 104 and acquiring real-time images during the treatment process. Sensor 122 may also be a laser collimated to also be focused on one or more of the samples 104. For example, due to quasi-elastic light scattering by the dispersed particles in the sample well, the hydrodynamic diameter can be determined from the correlation length of the intensity fluctuation which are measured as a function of the scattering angle. One or more detectors (not shown) tuned to the laser wavelength could then be arranged at appropriate angles in one or both trays 106, 116.

In one embodiment (not shown), a transmittance photometer can be employed whereby collimated laser light is incident on the sample, and scattered light is measured in transmission by blocking the intensity of the collimated beam. The excitation light may be coupled to the sample by free space optics or by an optical fiber. The scattered light may be coupled out in a similar manner.

Other details of transducer characteristics, waveform selection, process timing, and positioning of the sample in the treatment bath relative to the acoustic energy source are described, for example, in commonly assigned U.S. Pat. No. 6,948,843, the entire contents of which are incorporated herein by reference.

The material from which the sample tray, such as the micro-titer plate, is constructed should be selected so as to absorb as little acoustic energy as possible and, ideally, should have an acoustic impedance similar to water. The material should also be relatively thin for maximizing ultrasound transmission.

Standard polystyrene or polypropylene micro-well plates, such as plates with 96 wells, have a wall and bottom thickness of approximately 1 mm. Tests with a micro-well plate oriented horizontally and exposed to acoustic energy from a needle-tip transducer submerged in water resulted in approximately 70% transmission through polystyrene.

As mentioned above, the processing systems according to the invention are particularly suited for focused acoustic treatment of samples placed in wells of micro-plates. Modem analytical laboratories, in particular pharmaceutical laboratories, have a throughput of hundreds or even thousands of samples per hour, which can advantageously be mixed or otherwise homogenized, solubilized, or conditioned before physical or chemical analysis. The processing system 300 may be a stand-alone system, but may optionally be a part of a robotic analytical station with Pick & Place and conveyor systems transporting the samples between the stations. Such systems may advantageously be equipped to handle a mix of plate/vial designs, such as 48, 384, 1536 well plates and proprietary designs. Optionally, pre-treatment sealing as described above with reference to FIGS. 3 and 5 can be permanent (i.e., the sealing material remains in place after acoustic processing, e.g., during subsequent storage) or temporary (i.e., the sealing material is removed after acoustic processing), e.g., depending on whether direct access to the sample itself is later required. In certain embodiments, the sealing material is selected to be compatible with the sample withdrawal apparatus of the analytic station. For example, a thin film that can be punctured by a needle may be used as a sealing material in embodiments where sample is collected for analysis using a syringe or similar needle-tipped sampler.

In processing system embodiments above and in others consistent with the invention, containers for samples such as tubes, vials, wells, tube racks, vial racks, or well plates, which are coupled with a fluid, such as water, to one or more transducers may have residues of the fluid disposed on the outer surface of the container after removal from the liquid. As the container is being transferred, the residual liquid may drip off of the container. These drops may contaminate other containers, surfaces, or apparatus. After several such transfers, drops of fluid may accumulate in certain areas. Thus, the processing steps in embodiments consistent with this invention may include steps to remove the residual fluid from the surface of the container. In some embodiments, the container may be tapped on or shaken over a pad or other surface in order to remove the residual fluid. Alternately, the container may be placed over a vacuum or other appropriate device that can suction the residual fluid off of the container. Alternatively, the container may be contacted with an absorbent material, such as a cloth or paper towel to wipe away residual fluid. Such absorbent material may be configured as a continuous belt or a scrolling system so that unused or refreshed material is used to clean the containers each time. Alternately, the container may allowed to air dry, optionally with the assistance of application of a vacuum, fans, and/or hot air, after separation from the fluid bath. Subsequent to drying, the container can be carried to the next workstation for subsequent treatment or processing.

In other embodiments, alternate non-fluidic coupling means may be used. By way of examples, a material with a gel consistency or rubber consistency, such as silicon rubber, may be used and optionally encapsulated in membrane 210 (FIG. 2), for example, if the material might otherwise adhere to sample containers.

Returning now to FIG. 3, sample or plate 302*a* may include a slot, notch, projection or another suitable keying feature 322 for proper orientation and alignment in processing station 300 or any other type of processing equipment. The keying feature 322 can engage with a complementary keying feature (not shown) provided, for example, on the surface transmitting the acoustic energy, such as membrane 210. This can prevent plates from being inserted with a wrong orientation, or can prevent insertion of plates not intended or approved for use with the station 300. Alternatively, or in addition, plate 302*d* may include other identification or tracking means 324, such as a barcode, logo, and/or an RFID tag. Since station 300 can, as discussed above, be controlled by a controller 310, information read from the identification/tracking means 324 may be used in conjunction with the data storage device 614 for recognizing samples, accessing a treatment protocol associated with the particular samples, and/or establishing and/or updating the process history of samples.

Information connected with the keying feature 322 and/or the identification and tracking means 324 may be transmitted to the controller 610 to select the intended sample for processing, to properly align or orient the sample tray in the processing station, to track samples during processing, to apply the intended processing steps to the samples, such as delivery of the intended amount of acoustic energy at the intended frequency with proper timing, and other control functions described with reference to FIG. 6. Positioning of the sample tray 102 in the station 300 may be aided, for example, by mechanical sensors, optical sensors, laser beams, electromagnetic sensors, capacitive sensors, acoustic sensors, and the like, located on or in the station 300 and cooperating with the tray 102. It will be understood that many of these sensors and sensor functions can also be controlled by the controller 610 (FIG. 6). In certain embodiments, the controller may activate the transducer or transducers only when a sample tray 102 is detected in an appropriate position for treatment, and deactivate the transducer or transducers either after treatment is completed (e.g., as determined by sensor feedback or completion of a programmed treatment protocol), when the sample tray 102 has moved to a position out of alignment with the transducer or transducers, or at any other suitable time.

In embodiments consistent with the invention, the processing steps may involve treating each of a plurality of samples with acoustic energy for substantially the same length of time with substantially the same level of power. In alternate embodiments, varying amounts of time and/or power may be used for each of the samples. The length of time and level of power for each sample may be a function of the amount of that sample to be treated, the condition of the sample prior to treatment, or a protocol preassociated with the sample. For example, prior to treatment of each sample, the amount of that sample may be gauged or estimated. In some embodiments, the volume of each sample is acoustically determined prior to treatment. By way of example, a system consistent with the invention may include a plurality of tubes or wells of a sample tray each containing varying amounts of sample, and each having a transducer placed near or in contact with the bottom of the tube/well. The transducers acoustically characterize or map the volume of sample in each of the plurality of test tubes. The characterization may involve pinging the tube/ sample, and measuring or gauging a return signal from the tube/sample. Subsequent to this characterization, each of the tubes may be treated in a separate step with an energy dose appropriate for the volume of sample for that tube. By way of example, a 100 microliter (1 μl) solution may require a 1 second dose of acoustic energy for treatment, whereas a 500 μl solution may require a 5 second dose. The transducer used for treatment may be the same as the transducer used for volume characterization, but in alternate embodiments a separate transducer is used for processing the sample after volume measurement has been completed. This may be accomplished, for example, by simultaneously having both transducers in a coupling relationship with the sample, or by repositioning the sample from a coupling relationship with one transducer to a coupling relationship with the second transducer.

In an exemplary embodiment similar to the embodiment depicted in FIGS. 1 and 2, two transducers 118, 120 may be placed near the bottom of each sample 104. By way of example, each sample 104 may be associated with an outer transducer 120 which is substantially doughnut-shaped, and an inner transducer 118 located within the hole of the doughnut-shaped outer transducer 120. The inner transducer 118 may be used for sample interrogation, such as volume measurement or particle detection, while the outer transducer 120 may be used for treatment of the sample 104, or vice versa. In one embodiment, the inner transducer 118 transmits acoustic waves at a frequency between about 1 MHz and about 20 MHz, for example at 5 MHz, and the outer transducer 120 transmits acoustic waves in a frequency between about 100 kHz and about 1 MHz, for example at 500 kHz. In some embodiments, the acoustic waves used for volume characterization are transmitted at a higher frequency and lower power than the acoustic waves used for treatment of the sample. The volume characterization step and sample treatment step may be time-multiplexed. The treatment step may include any one or more of the treatments described herein, including, for example, heating, fluidizing, mixing, stirring, disrupting, redissolving, homogenizing, enhancing a reaction in, and/or sterilizing the sample. In some embodiments, illustrated schematically in FIG. 1, the acoustic elements may be confocal and coaxial, in others they may be confocal but located on axes relative to the position of sample 104 which subtend an angle α, for example an angle of ~90°. For example, the treatment transducer 118 may be coaxial with the sample 104 transmitting energy through the bottom of the tray 102 while another transmitting transducer 121 may be at an angle α and transmitting/receiving through the side of the sample 104 for interrogation. For other types of analysis (e.g., acoustic scattering), an additional side receiving transducer 123 (shown as located behind the inner tray) may be at an angle β, wherein β may be ~90°, in relation to the side transmitting transducer 121; this arrangement may also be confocal.

Figure 7:
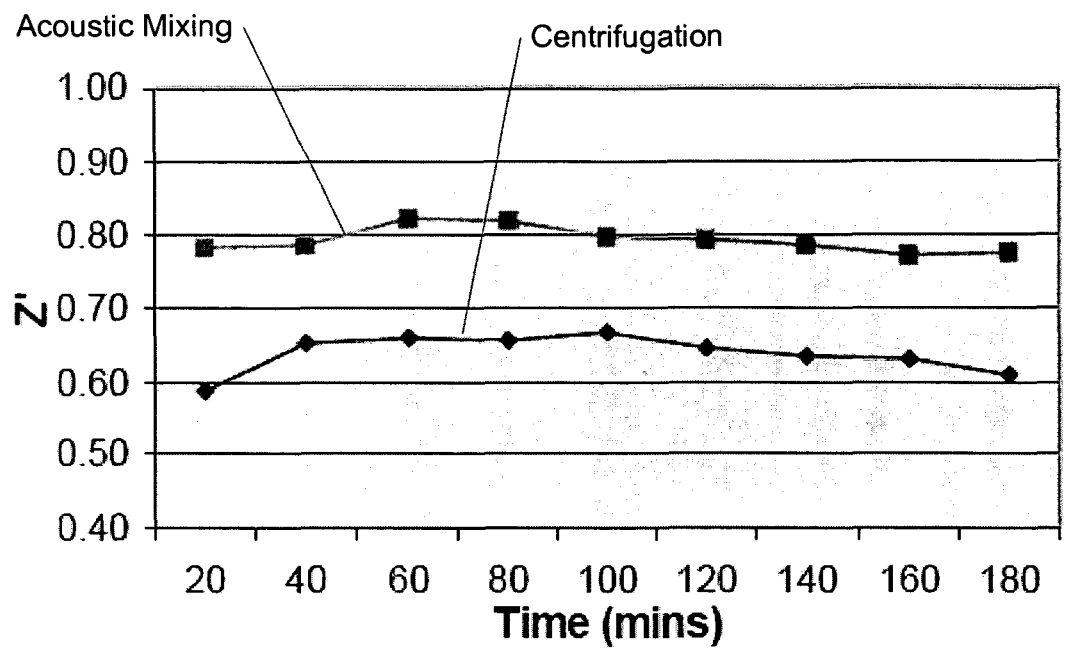
FIGS. 7 and 8 are diagrams showing experimental results for compound processing with focused acoustic energy.
Figure 8:
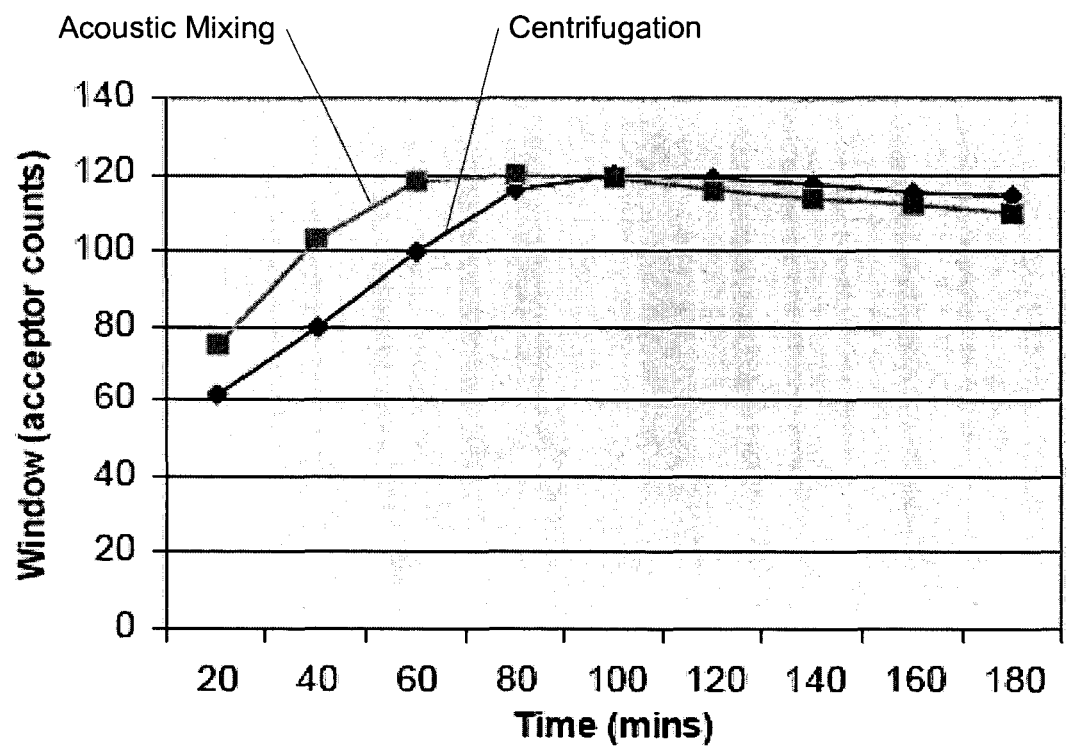

FIGS. 7 and 8 summarize experimental results obtained with acoustic mixing in 1536 white Greiner plates with 50 nl/well of compound with a total assay volume of 8 μl. The assay protocol involved four 2 μl reagent additions using Synquad and Cybiwell, with a centrifugation step after each addition. The final centrifugation step was replaced with acoustic mixing using a line-based acoustic transducer operating at 800 kHz. The data shown in FIG. 5 show an overall improvement in assay performance in terms of Z' of 0.2 (from 0.6 to 0.8; or 33%) for a cAMP HTRF assay. Z-prime (or Z') is a measure of the overall assay quality, relating the variability of positive and negative readings to the difference between the positive and negative levels. Z' can have a maximum value of 1.0, whereas a Z' value below 0.5 is considered unacceptable. A similar improvement in Z' was observed for a Kinase assay (not shown). The observed average increase in Z' can be attributed to an improvement in signal window, and a reduced standard deviation of both signal and background.

As illustrated in FIG. 8, the time it takes to reach equilibrium is also reduced by approximately 25% compared to centrifugation. The assay reaches its maximum signal more quickly, in the depicted example around 60 minutes instead of the 80 minutes required without acoustic mixing. Commonly used techniques (e.g., not based on acoustic mixing) are often ineffective due to high surface tension which has the effect of keeping the reagents separated, and also retaining bubbles. Focused acoustic energy is also expected to improve mixing of SPA bead based assays by retaining a uniform suspension during aliquotting, reacting, and analysis.

By way of example, although the illustrative embodiments have been described in conjunction with compound management and high throughput chemistry for compound dissolution, this need not be the case. The process is especially beneficial for high-throughput compound dissolution and resolution, such as primary dissolution of dried and/or lyophilized compounds and/or extracts; cell lysis-mammalian, insect, *E-coli*, plant; high-throughput chemistry and screening; drug metabolism and pharmacokinetics; RNA extraction-homogenization of biological tissue, and/or tissue homogenization for proteomic studies. It can also be used for RNA extraction, nucleic acid hybridization, and ADMEtox.

The invention contemplates all operable combinations of the features, aspects, and embodiments of the invention disclosed herein. Furthermore, the invention contemplates embodiments including all operable combinations with the subject matter disclosed in U.S. application Ser. No. 10/777,014, filed Feb. 11, 2004, and entitled "Apparatus and Methods for Controlling Sonic Treatment", U.S. application Ser. No. 11/167,934, filed Jun. 27, 2005, and entitled "Methods and Apparatus for Acoustically Controlling Liquid Solutions in Microfluidic Devices" and U.S. application Ser. No. 11/295,372, filed Dec. 5, 2005, and entitled "Methods and Systems for Modulating Acoustic Energy Delivery." The disclosures of each of the foregoing applications are hereby incorporated by reference in their entirety.

While there has been described herein what are considered to be exemplary and preferred embodiments of the invention, other modifications and alternatives of the inventions will be apparent to those skilled in the art from the teachings herein. All such modifications and alternatives are considered to be within the scope of the invention.

We claim:

1. An apparatus for processing a sample using acoustic energy, the apparatus comprising:
   a vessel for holding the sample;
   an acoustic energy source spaced from and exterior to the vessel for providing acoustic energy substantially converging in a focal zone proximate to the sample in the vessel, the acoustic energy having a frequency of between about 100 kilohertz and about 100 megahertz and having a focal zone having a width of less than about 2 centimeters;
   a first medium for coupling acoustic energy to the sample in the vessel;
   a second medium disposed adjacent to the vessel, the second medium for coupling the acoustic energy to the sample in the vessel, wherein the second medium comprises a semi-solid material that is in a semi-solid state when the semi-solid material is at room temperature;
   a sensor that senses a physical parameter of the sample in the vessel; and a controller that controls the acoustic energy source and the acoustic energy at the focal zone based on information from the sensor regarding the physical parameter.

2. The apparatus of claim 1, wherein the physical parameter is a sample volume and the acoustic energy is controlled by the controller based on the sample volume.

3. The apparatus of claim 1, wherein the physical parameter is a sample temperature and the acoustic energy is controlled by the controller based on the sample temperature.

4. The apparatus of claim 1, wherein the physical parameter is a concentration of particulate matter in the sample and the acoustic energy is controlled by the controller so as to comminute the particulate matter.

5. The apparatus of claim 1, wherein the sensor senses a physical parameter of the sample before, during or after processing with the acoustic energy, or a combination thereof.

6. The apparatus of claim 1, wherein the first medium comprises a solid or semi-solid material.

7. The apparatus of claim 1, wherein the semi-solid material has a transmissivity for acoustic energy of at least 80% compared to water at an emission wavelength of the acoustic energy source.

8. The apparatus of claim 1, further comprising a cover facing the sample for protecting the sample from contamination.

9. The apparatus of claim 1, wherein the acoustic energy source is disposed in the first medium and is capable of transmitting acoustic energy to the sample in the vessel, and the second medium is disposed between the first medium and the sample in the vessel.

10. The apparatus of claim 1, further comprising a peripheral seal adapted to seal a space between the vessel and the second medium in an area where the second medium contacts the vessel, wherein a vacuum line connects the space to a vacuum source.

11. The apparatus of claim 9, further comprising a pressure source for applying an external pressure to the first medium for urging the second medium into contact with the vessel.

12. The apparatus of claim 1, wherein the second medium comprises silicone gel, elastomeric polyurethane or thermoplastic elastomer, or a combination thereof.

13. The apparatus of claim 1, wherein the vessel comprises a plate having a plurality of wells adapted to receive an assay.

14. The apparatus of claim 8, wherein the cover comprises a sealing station, said sealing station providing a sealing material to temporarily or permanently seal the sample within the vessel.

15. The apparatus of claim 14, wherein the controller controls operation of the sealing station.

16. The apparatus of claim 14, wherein the sealing material comprises at least one of a foil, film, wrap, a cover, and a plug.

17. The apparatus of claim 1, wherein the sensor comprises an acoustic sensor positioned confocally and coaxially with the acoustic energy source.

18. The apparatus of claim 1, wherein the sensor comprises an acoustic sensor positioned at an angle with respect to a beam direction of the acoustic energy source.

19. The apparatus of claim 1, further comprising an additional transmitting transducer oriented at a first angle with respect to a beam direction of the acoustic energy source and an acoustic sensor positioned at a second angle with respect to a beam direction of the additional transmitting transducer.

20. The apparatus of claim 19, wherein the additional transmitting transducer and the acoustic sensor are located in a plane which is perpendicular to the beam direction of the acoustic energy source.

21. The apparatus of claim 1, wherein the vessel comprises a sample identification marker.

22. The apparatus of claim 21, wherein the sample identification marker comprises a barcode, a logo, an Rfid tag, or a combination thereof.

23. The apparatus of claim 1, wherein the vessel comprises a sample key cooperating with a complementary key disposed on the apparatus for preventing insertion of an inappropriate sample.

24. The apparatus of claim 1, further comprising a database included in or operatively connected to the controller, said database storing processing data for the sample.

25. The apparatus of claim 24, wherein the controller controls delivery of the acoustic energy to the sample based on the stored processing data.

26. An apparatus for high-throughput processing of at least one sample using acoustic energy, the apparatus comprising:
    a vessel for holding the at least one sample;
    an acoustic energy source spaced from and exterior to the vessel for providing acoustic energy substantially converging in a focal zone proximate to the at least one sample in the vessel, the acoustic energy having a frequency of between about 100 kilohertz and about 100 megahertz and having a focal zone having a width of less than about 2 centimeters;
    a first medium for coupling the acoustic energy to the at least one sample for processing of the at least one sample;
    a second medium disposed adjacent to the vessel, the second medium for coupling the acoustic energy to the at least one sample in the vessel, wherein the second medium comprises a semi-solid material that is in a semi-solid state when the semi-solid material is at room temperature;
    a sensor for interrogating the at least one sample to measure an initial status of the at least one sample; and
    a controller for controlling delivery of the acoustic energy to the at least one sample, said controller executing a processing sequence appropriate to the initial status, periodically or continuously interrogating the at least one sample to determine a desired outcome of the processing sequence, and adjusting or terminating the processing sequence when the processing sequence produces the desired outcome.

27. The apparatus of claim 26, wherein the processing sequence is adjusted by moving the at least one sample into or out of the focal zone.

28. The apparatus of claim 26, wherein the processing sequence is terminated by moving the at least one sample out of the focal zone and moving another at least one sample into the focal zone and repeating a processing sequence.

29. The apparatus of claim 26, wherein interrogation of the at least one sample provides a measurement of a meniscus position of the at least one sample.

30. The apparatus of claim 26, wherein interrogation of the at least one sample provides a measurement of a concentration of particulates in the at least one sample.

31. The apparatus of claim 26, wherein the processing sequence includes a measure of the acoustic energy delivered to the at least one sample, an application time of the acoustic energy, a timing pattern for the application of the acoustic energy, or a frequency or a frequency modulation of the acoustic energy, or a combination thereof.

32. A method of processing sample arrays including at least one sample using acoustic energy, comprising:
    interrogating the at least one sample in a vessel to measure a status of the at least one sample in the vessel;

coupling a transducer of focused acoustic energy to the at least one sample in the vessel through a first medium and a second medium, the second medium being disposed adjacent to the vessel and the second medium comprising a semi-solid material that is in a semi-solid state when the semi-solid material is at room temperature, and wherein the acoustic energy has a frequency of between about 100 kilohertz and about 100 megahertz and a focal zone having a width of less than about 2 centimeters;

executing a processing sequence appropriate to the status to deliver acoustic energy to the at least one sample, periodically or continuously interrogating the at least one sample to detect the presence or absence of a desired condition of the at least one sample, and adjusting or terminating the processing sequence when the desired condition is detected.

33. The method of claim 32, wherein executing the processing sequence comprises delivering acoustic energy to the at least one sample, setting a time for delivering the acoustic energy, setting a timing pattern for delivering the acoustic energy, or setting a frequency or a frequency modulation for delivering the acoustic energy, or a combination thereof.

34. The method of claim 32, wherein terminating the processing sequence comprises coupling the focused acoustic energy to another one of the at least one sample and repeating the same or another processing sequence.

35. The method of claim 32, wherein interrogating the at least one sample comprises measuring a meniscus position of the at least one sample, a sample temperature, or a concentration of particulates in the at least one sample, or a combination thereof.

36. The method of claim 32, further comprising temporarily or permanently sealing the at least one sample.

37. The method of claim 32, further comprising transmitting to the at least one sample an acoustic interrogation beam and detecting an acoustic response signal from the at least one sample at a location having an angular offset from the acoustic interrogation beam.

38. The method of claim 32, further comprising applying an active or a passive identifier to the at least one sample and selecting the at least one sample for processing or aligning the at least one sample in relation to the focused acoustic energy based on the identifier.

39. The method of claim 1, wherein the semi-solid material and a seal surround and contact a bottom portion of the vessel.

* * * * *